US012650037B2

(12) United States Patent
Hughes

(10) Patent No.: US 12,650,037 B2
(45) Date of Patent: Jun. 9, 2026

(54) RESTRAINT FOR HUMANE TREATMENT OF DETAINEE AND METHOD OF USING THE SAME

(71) Applicant: Justin Hughes, Lebanon, OH (US)

(72) Inventor: Justin Hughes, Lebanon, OH (US)

( * ) Notice: Subject to any disclaimer, the term of this patent is extended or adjusted under 35 U.S.C. 154(b) by 18 days.

(21) Appl. No.: 18/778,895

(22) Filed: Jul. 19, 2024

(65) Prior Publication Data

US 2025/0012117 A1     Jan. 9, 2025

Related U.S. Application Data

(63) Continuation-in-part of application No. 17/448,043, filed on Sep. 18, 2021, now abandoned.

(60) Provisional application No. 63/080,696, filed on Sep. 19, 2020.

(51) Int. Cl.
| | |
|---|---|
| *E05B 75/00* | (2006.01) |
| *A61B 5/00* | (2006.01) |
| *A61B 5/0205* | (2006.01) |
| *A61B 5/024* | (2006.01) |

(52) U.S. Cl.
CPC ............ *E05B 75/00* (2013.01); *A61B 5/0004* (2013.01); *A61B 5/02055* (2013.01); *A61B 5/4266* (2013.01); *A61B 5/6825* (2013.01); *A61B 5/742* (2013.01); *A61B 5/746* (2013.01); *A61B 5/7475* (2013.01); *A61B 5/02438* (2013.01); *A61B 2560/0252* (2013.01); *A61B 2562/0271* (2013.01); *A61B 2562/06* (2013.01)

(58) Field of Classification Search
CPC ... E05B 75/00; A61B 5/0004; A61B 5/02055; A61B 5/4266; A61B 5/6825; A61B 5/742; A61B 5/746; A61B 5/7475; A61B 5/02438; A61B 2560/0252; A61B 2562/0271; A61B 2562/06
USPC ............................................................. 70/16
See application file for complete search history.

(56) References Cited

U.S. PATENT DOCUMENTS

| | | | | | |
|---|---|---|---|---|---|
| 4,089,195 | A * | 5/1978 | Lai | ........................... | E05B 75/00 |
| | | | | | 361/232 |
| 7,629,892 | B1 * | 12/2009 | DeMott | ................... | E05B 45/06 |
| | | | | | 70/423 |
| 8,353,183 | B1 * | 1/2013 | Lofgren | ................. | E05B 75/00 |
| | | | | | 70/16 |

(Continued)

FOREIGN PATENT DOCUMENTS

| | | | | | |
|---|---|---|---|---|---|
| CN | 109113459 | A * | 1/2019 | ............. | E05B 75/00 |

*Primary Examiner* — Nathan Cumar
(74) *Attorney, Agent, or Firm* — Adam F. Mathews; Daniel F. Nesbitt; Nesbitt IP LLC

(57) ABSTRACT

The invention relates to a restraining device comprising a restraint for physically constraining movement of at least a portion of a detainee's body. The restraint further has a tightness-adjusting component coupled to the restraint and a control system coupled to the tightness-adjusting component. The control system is configured to cause the tightness adjustment component to adjust the tightness of the restraint upon the detainee when a predetermined condition occurs. There is a sensor in communication with the control system, and the sensor is configured to detect whether the detainee enters into a medical or physical condition requiring a response; the control system is configured to adjust the tightness of the restraint to the detainee when the sensor indicates the detainee needs a different level of tightness regarding the restraint.

19 Claims, 6 Drawing Sheets

(56) References Cited

U.S. PATENT DOCUMENTS

| | | | |
|---|---|---|---|
| 11,434,668 B1 * | 9/2022 | Wriggle | G01S 19/14 |
| 2010/0206017 A1 * | 8/2010 | Garibaldi | E05B 75/00 |
| | | | 70/16 |
| 2012/0118027 A1 * | 5/2012 | Shulman | E05B 75/00 |
| | | | 70/16 |
| 2012/0298119 A1 * | 11/2012 | Reese | E05B 75/00 |
| | | | 128/869 |

* cited by examiner 101                                                    100

200

1010                                                    105

RESTRAINT FOR HUMANE TREATMENT OF DETAINEE AND METHOD OF USING THE SAME

CROSS REFERENCE TO OTHER APPLICATIONS

This application is a continuation-in-part of U.S. patent application Ser. No. 17/448,043, filed on Sep. 18, 2021, which claims priority to U.S. Provisional Patent Application No. 63/080,696 filed on Sep. 19, 2020, both of which are incorporated by reference in their entireties.

FIELD OF THE INVENTION

Embodiments of the invention relate to restraint systems, particularly to electronic systems affixed or integrated into a restraint system to monitor, record, and report an individual's vital signs.

BACKGROUND OF THE INVENTION

Restraint systems for detaining individuals have a long history, with the first recognizable metal handcuffs dating back to the Bronze and Iron Ages. However, the design and functionality of these systems have remained largely unchanged for over a century. In the fast-paced and evolving world of the 21st century, there is a pressing need for more advanced restraint systems that can address the unique challenges faced by arresting authorities. Current restraint systems lack the capability to monitor the vital signs of individuals being detained, which is crucial for public health and safety.

SUMMARY OF THE INVENTION

The present invention is a humane restraint device comprising a handcuff restraint system with at least two cuff loops connected by a chain, where each cuff loop further comprises a ratchet mechanism paired with a latching mechanism; a body removably affixed to at least one cuff loop comprising at least one sensor, where the at least one sensor is configured to monitor the heart rate of a human being; and a tension monitor configured to measure and detect tension and adjust the level of restraint applied to the human being based on detected tension.

An additional embodiment of the invention has a sensor that comprises at least one sensor selected from the group consisting of electrocardiogram (ECG) sensors, pulse oximeters, and photoplethysmography (PPG) sensors. Additionally, the embodiment of the invention may comprise a perspiration sensor. Embodiments with such sensors may further comprise a wireless communication module for transmitting heart rate data to an external device. Additionally, or alternatively, the humane restraint device may have a control unit that is programmed with algorithms to determine an optimal restraint level based on heart rate and tension data.

An additional embodiment of the invention comprises a wireless communication module for transmitting heart rate data to an external device. This embodiment may further comprise the sensor selected from the group consisting of electrocardiogram (ECG) sensors, pulse oximeters, and photoplethysmography (PPG) sensors.

In further embodiments of the humane restraint device of the heart monitor is configured to generate an alert signal when an abnormal heart rate is detected. Additionally or alternatively, an alarm is integrated into the restraint system, wherein the alarm is configured to generate an alert when an abnormal heart rate is detected. In a related embodiment, the alarm further alerts if the body is removed from one or more cuff loops.

In an additional embodiment of the humane restraint, the tension monitor is integrated into the interior surface of the cuff loop of the restraint. In a related embodiment, the tension monitor is configured to measure tension at multiple points along the restraint. In further related, embodiments, the cuff loops may comprise sensors at multiple locations.

In an additional embodiment of the invention, the humane restraint further comprises a display integrated on the restraint mechanism. In related embodiments, the display further comprises a user interface to control the restraint mechanism.

In an additional embodiment of the invention, the humane restraint further comprises at least one thermometer at the sensor locations. The at least one thermometer may be configured to measure the ambient temperature, configured to measure the temperature of the restrained person, or both. In a related embodiment, at least one thermometer is configured to measure the temperature of the restrained person, and the processor integrates the difference between the temperature of the ambient temperature and the temperature of the restrained person in its algorithms to determine an optimal restraint level. In a further embodiment, the cuff loops comprise sensors at multiple locations.

DETAILED DESCRIPTION OF THE INVENTION

Figure 2:
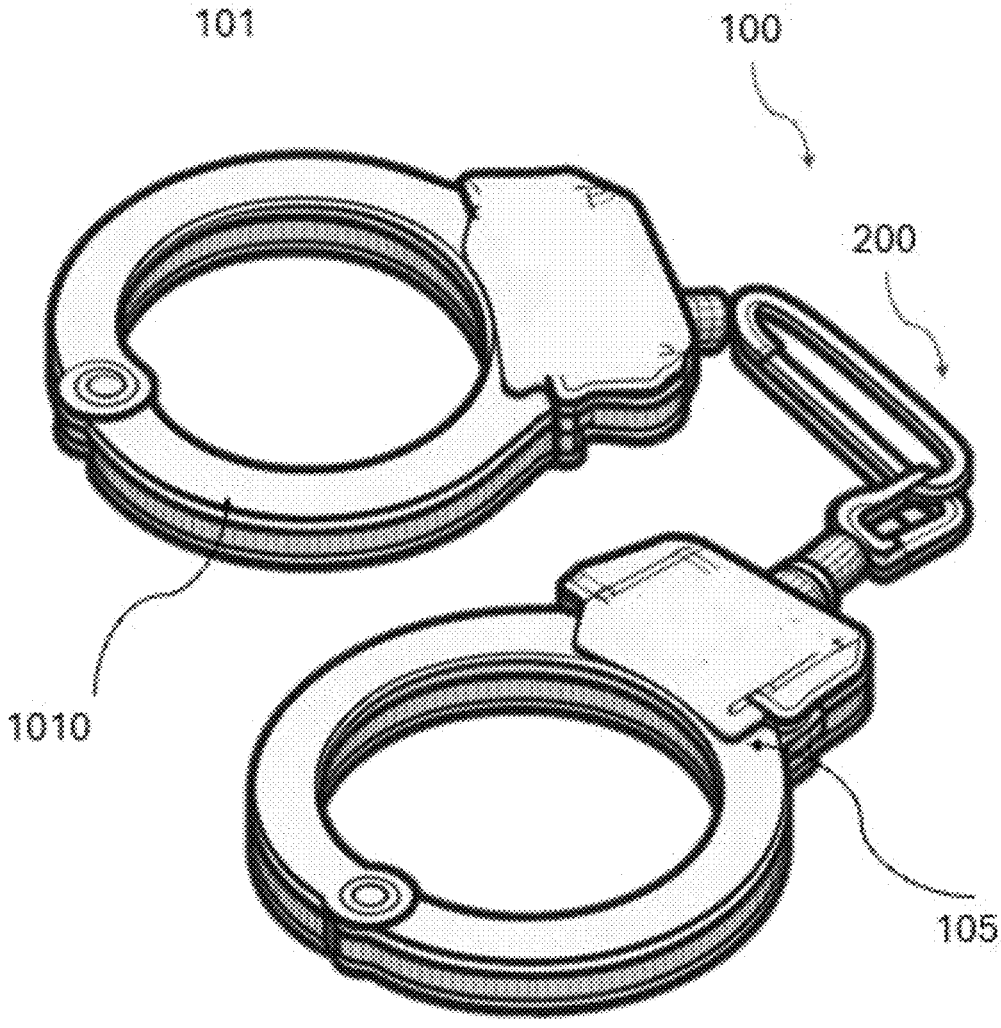
FIG. 2 shows a prior art restraint system (Peerless style handcuff) as an example of how the invention can be implemented into existing systems.

FIG. 2 shows the state of the art, with a standard wrist restraint with the following elements.

The first component of the handcuff restraint system 100 is a loop 101 designed to encircle and secure one wrist of the individual. This cuff loop 101 typically includes a ratchet mechanism 1010 for adjustable closure and a latching mechanism 105 for secure engagement. Correspondingly, a second cuff loops 102 mirrors the design of the first cuff loop 101 and is intended to encircle and secure the other wrist of the individual. Both cuff loops 101, 102 are configured to be comfortable yet secure, preventing easy tampering or removal.

Another crucial element is a central link or chain 200 that connects the first cuff loop 101 to the second cuff loop 102, allowing limited movement while still restricting the detainee's ability to separate their hands. This link or chain 200 is typically made of a durable material, such as metal, to ensure strength and security. There is also a key entry point 103 wherein a key can enter to disengage a latching mechanism 105.

Incorporated within each cuff loop is a ratchet mechanism 1010, 1020. This mechanism allows for the adjustment of the cuff's tightness, ensuring a snug fit around the detainee's wrists. The ratchet mechanism 1010, 1020 may include teeth or grooves for incremental adjustments.

The latching mechanism 105 secures the cuff loops 101, 102 in a closed position once placed around the individual's wrists. This mechanism 105 is designed to prevent accidental or unauthorized release and may include a lock for added security.

Figure 1:
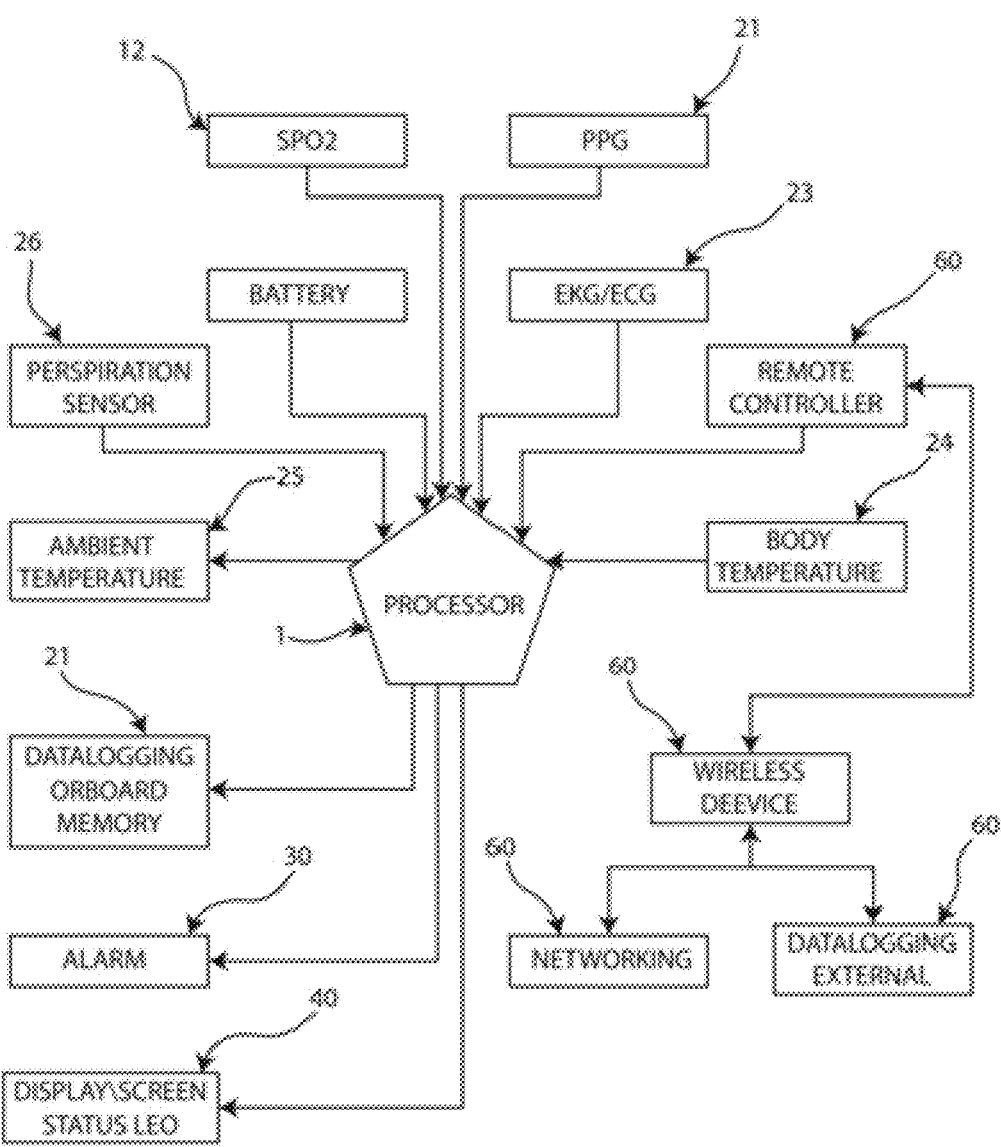
FIG. 1 shows a diagram that illustrates the processor with preferred input/outputs, capable of receiving various vital sign data such as PPG, SPO2, EKG/ECG, body temperature, ambient temperature, and perspiration sensor. The invention supports wireless charging and a detachable rechargeable battery. It can be controlled locally or remotely, with onboard and remote wireless data logging. The device networks with external devices, and optional displays report data.

FIG. 1 is a diagram that provides a comprehensive overview of the processor 1 and its preferred input/outputs, showcasing the device's capability to collect an array of vital sign data crucial for monitoring an individual's health during restraint.

Processor 1 is equipped to receive a diverse range of vital sign data through various input channels/sensors 20, with embodiments choosing one or more of the below:

Photoplethysmography (PPG) 21: The invention may incorporate one or more PPG sensors 21 to measure blood volume changes in the microvascular bed of tissue. This allows for the continuous and non-invasive monitoring of blood flow, providing valuable insights into heart rate variations and circulatory patterns.

Oxygen Saturation (SPO2) 22: One or more SPO2 22 sensors may be employed to gauge the oxygen saturation levels in the bloodstream. This data is pivotal for assessing the individual's respiratory function and overall oxygen-carrying capacity.

Electrocardiography (EKG/ECG) 23: In an exemplary embodiment, the processor 1 interfaces with one or more EKG/ECG sensors 23, enabling the recording of the electrical activity of the heart over time. This information is crucial for identifying irregular heart rhythms and potential cardiac issues.

Body Temperature 24: The invention incorporates sensors/thermometers 24 to monitor the individual's body temperature in real-time. Fluctuations in body temperature can be indicative of various health conditions, and this data contributes to a comprehensive health assessment.

Ambient Temperature 25: The processor is designed to receive data from ambient temperature sensors 25. This information is valuable in differentiating between changes in the individual's internal body temperature and external environmental factors.

Perspiration Sensor 26: The inclusion of perspiration sensors 26 allows for the non-invasive collection of data related to the individual's sweat composition. Changes in perspiration patterns can provide insights into stress levels, dehydration, and overall physiological responses.

The embodiment of the invention ensures a multi-faceted approach to vital sign monitoring, encompassing cardiovascular, respiratory, thermoregulatory, and stress-related parameters. The integration of these various sensors enhances the device's capability to provide a holistic assessment of an individual's health status during detention.

The processor 1, acting as the central hub, processes and analyzes this diverse set of vital sign data in real time. The resulting information not only serves immediate monitoring needs but is also logged for future reference and analysis. This comprehensive approach to data collection positions the invention as a cutting-edge solution for enhancing the safety and well-being of both the restrained individual and the authorities responsible for their detention.

Figure 3:
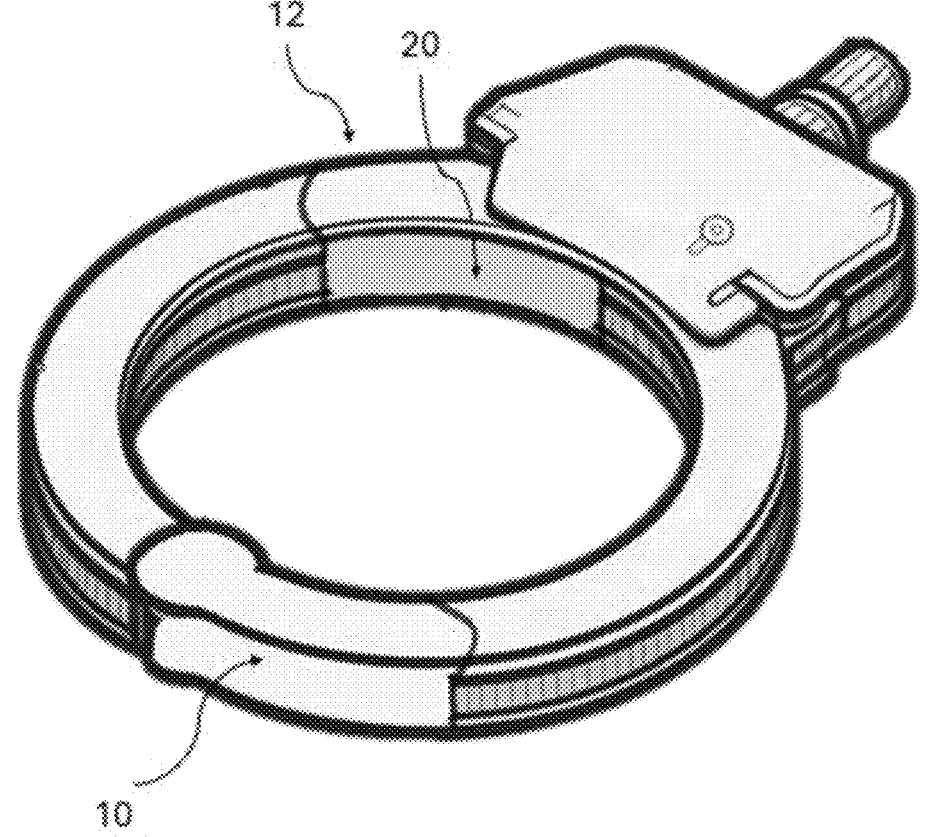
FIG. 3 depicts sensors on the lower and upper portions of the restraint for a display-less implementation, with data sent and displayed on a remote device.

FIG. 3 shows a preferred embodiment without a display screen 40. Sensors described above may be present anywhere along the interior circumference of the wrist restraint 100, or in exterior sensor location 10 or interior sensor location 12. These sensor locations 10, 12 may have any of the above vital sign sensors 20 as well as tension sensors. These tension sensors 20 may provide the level of tension within the cuff loops 101, 102.

Figure 6:
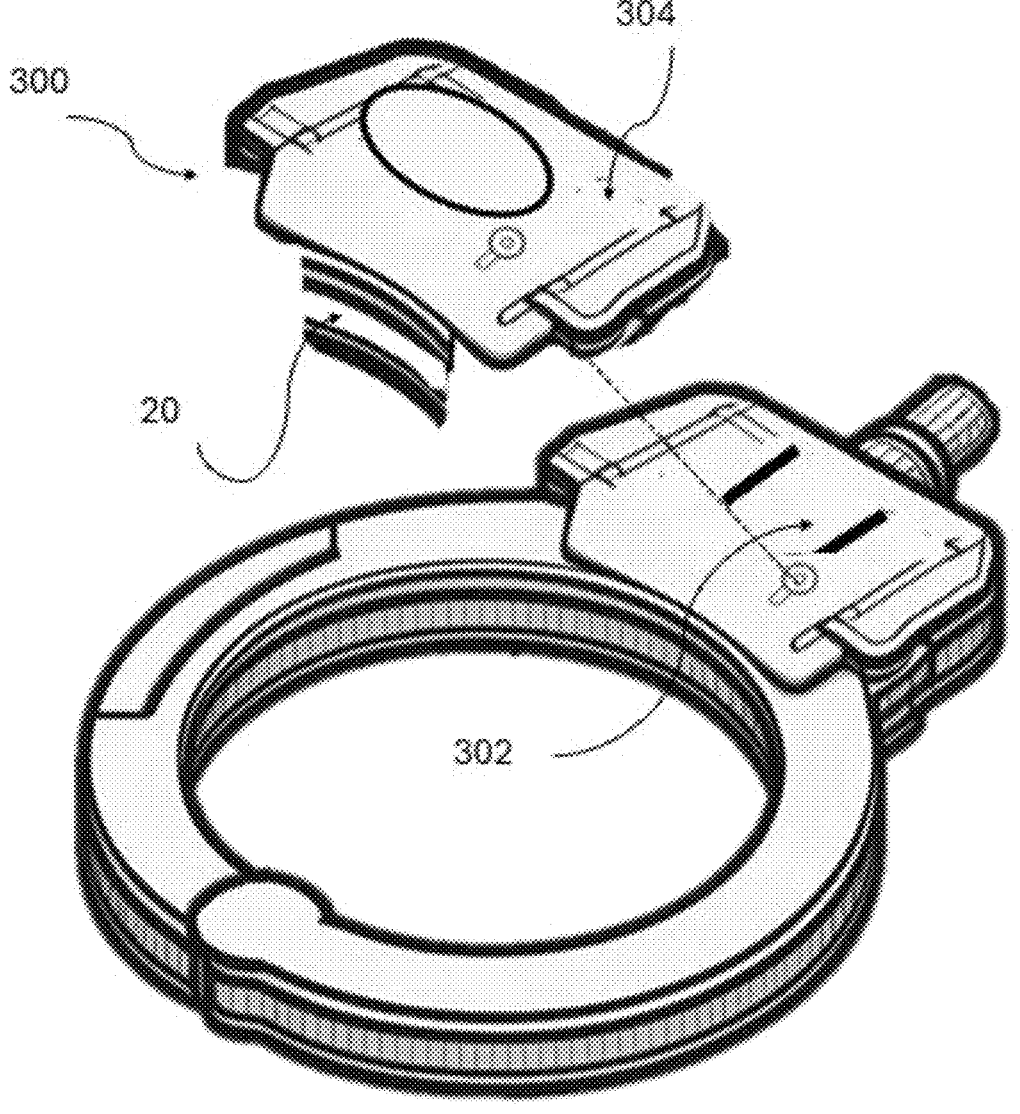
FIG. 6 shows a preferred embodiment with a retrofit assembly with a body that comprises a processor, sensors, and a display screen.

FIG. 6. shows a preferred embodiment with a retrofit assembly 300 with a body 304 that comprises the processor 1 and sensors 20 and a display screen 40. The retrofit assembly 300 comprises a body that can be affixed to standard handcuffs 100 as shown, for example, in FIG. 1. The body 304 may removably engage at engagement points 302 of the cuff loops 101, 102 to ensure secure fit. There may be sensors 20 within engagement points 302 connected to the processor 1 to alert the processor 1 if the retrofit assembly 300 is disconnected in any way from the cuff loops 101, 102.

In this way, existing owners of handcuffs 100 can add sensors 20 and/or the adjustable system and processor 1 to their handcuffs 100 without having to purchase fully new products. Further, the retrofit assembly 300 may be moved from one set of handcuffs 100 to another 100 by a technician.

Sensors 20 can be integrated into the cuff loops 101, 102. Alternatively, sensors 20 can be removable by a manufacturer or trained professional. In such embodiments, the sensor locations 10, 12 may have portions configured to mate with sensors 20. The sensors 20 would be unable to be removed by the restrained person or a general officer, to ensure the restrained person is treated humanely.

The processor 1 not only receives an extensive array of vital sign data through its various input channels but also serves as the command center for outputs and controls, ensuring a comprehensive and responsive restraint system.

Datalogging Onboard Memory 27: The processor 1 interfaces with an onboard memory system 27. This memory 27 is dedicated to logging and storing the vital sign data received from the sensors. The datalogging functionality allows for the creation of a historical record of the individual's health metrics, facilitating post-incident analysis and reference for medical professionals and law enforcement.

Alarm System 30: An integral part of the processor's 1 control capabilities is the alarm system. The invention is equipped with a visual and audible alarm mechanism 30 that can be activated based on predefined thresholds or specific events. This serves as an immediate alert for arresting authorities and emergency personnel in case of abnormal vital sign readings or potential health concerns. This alarm system 30 would also alert if the sensors 20 or processor 1 is removed from the cuff loops 101, 102.

Display Screen 40: The processor 1 has the ability to control a display screen. This optional but preferred feature provides a visual representation of the reported vital sign data. The display screen 40 can present real-time information about the individual's health status, enabling immediate assessment by law enforcement officials. Additionally, the screen 40 can convey alerts and notifications, ensuring that relevant parties are promptly informed of any critical health issues. The display screen 40 may be affixed directly to the body of the handcuffs 100 or alternatively to the retrofit assembly 300.

Figure 4:
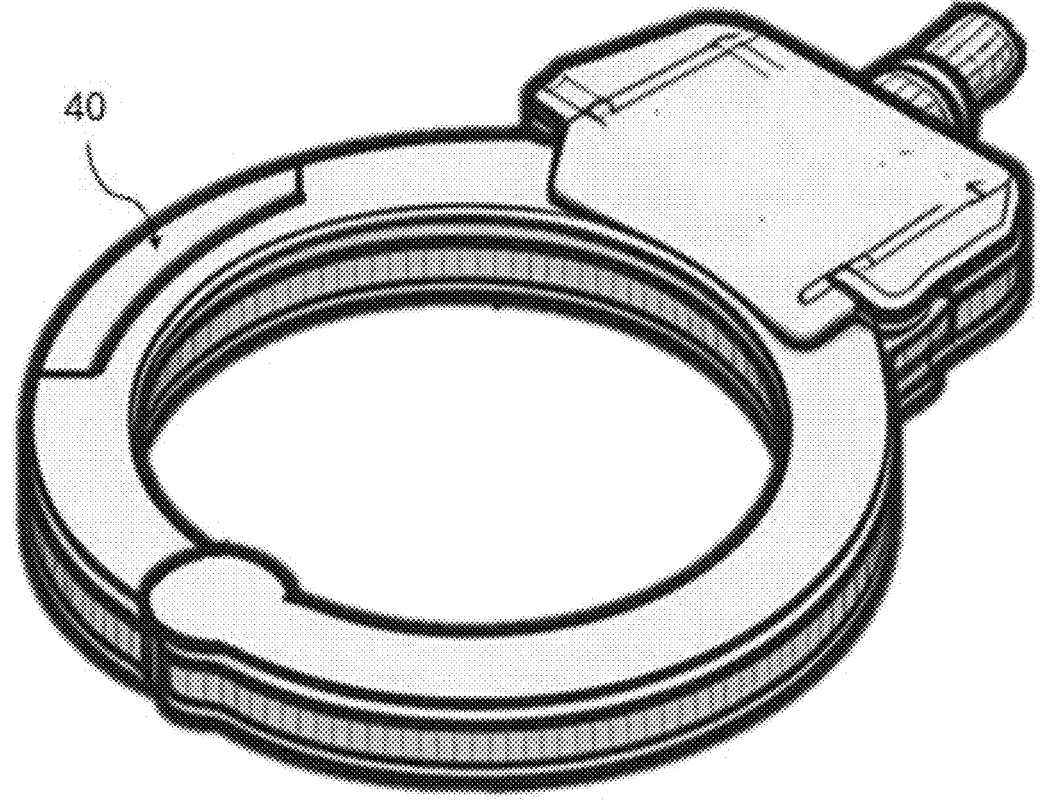
FIG. 4 displays the invention with a curved display and integrated sensor array.
Figure 5:
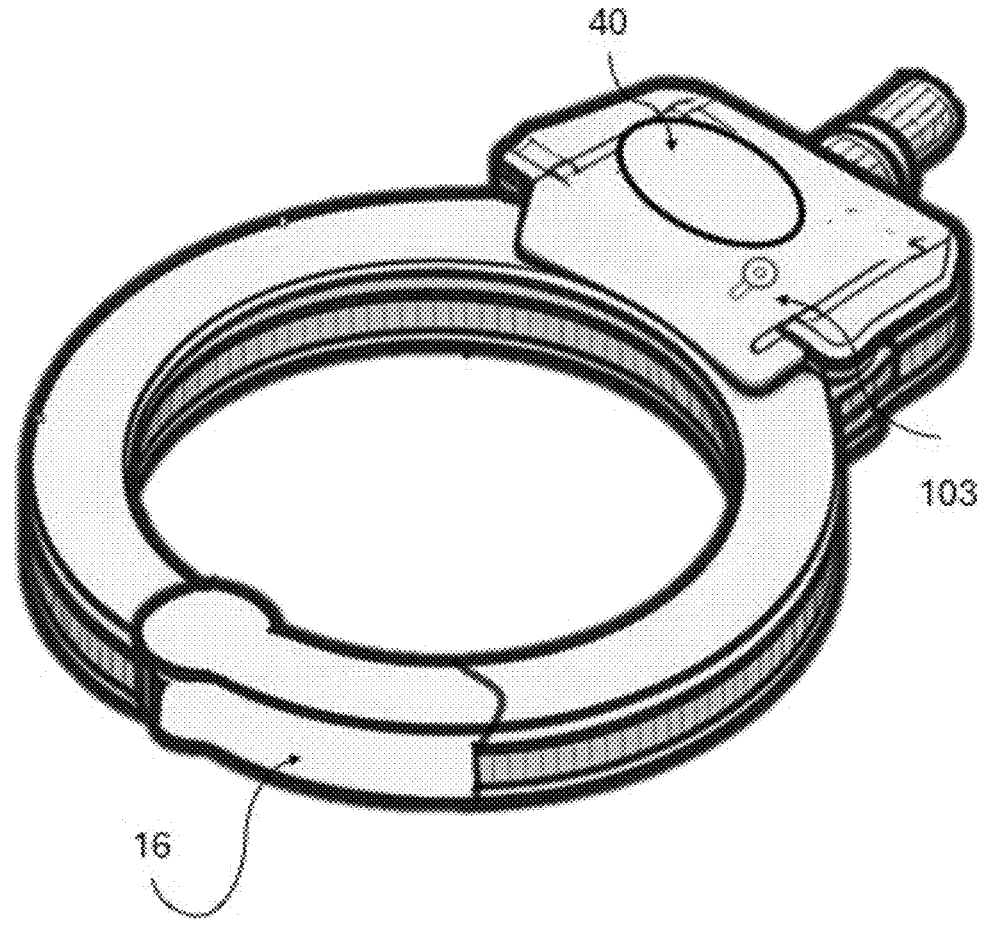
FIG. 5 illustrates the invention with sensors around the inner circumference of the restraint and a display on the body.

FIGS. 4 and 5 show alternative embodiments for display screens 40. In FIG. 4, the display screen 40 is curved along the exterior surface of the loop 101, 102 of the restraint device 100. FIG. 5 shows an alternative embodiment wherein the display screen 40 is on the body of the restraint device 100 near the key entry 103. This display screen 40 may be complex or simple, ranging from a simple on/off light system to a full video/computer display/LED display with full output.

Communication with Law Enforcement Officials 50: The processor 1 facilitates two-way communication with relevant law enforcement officials through the incorporation of networking capabilities 50. The device can transmit vital sign data, alarms, and status updates to designated personnel, enhancing situational awareness and enabling a more informed and responsive approach to detainment.

Remote Controller 60: The remote controller, representing a wireless device, plays a crucial role in providing input to the processor and maintaining two-way communication. The controller 60 may be wirelessly connected to the processor 1. The remote controller 60 can be operated by law enforcement or medical personnel and is capable of:

a. External Datalogging: The remote controller 60 allows external datalogging, facilitating the transfer and storage of vital sign data to external devices or databases. This feature supports comprehensive record-keeping and analysis beyond the immediate incident.

b. Networking: Through the remote controller 60, the processor 1 can establish communication with external devices, such as computers, handheld electronic devices, and/or other devices accessible by emergency medical technicians (EMTs) or law enforcement officials. This networking capability enables remote monitoring and real-time assessment by medical professionals.

c. Control Functionality: The remote controller 60 provides a means for external control of the restraint 100. This includes remotely adjusting settings, initiating specific actions (e.g., activating or deactivating alarms), and ensuring seamless integration with external systems. Further, using the information from the tension sensors 20, the restraint 100 can be loosened or tightened by the remote controller 60 to ensure humane treatment of the restrained person in accordance with the vital sign readings. The tension sensor 20 may measure tension at multiple points along the cuff loop 101, 102.

This advanced integration of outputs, controls, and remote communication elevates the invention beyond a traditional restraint system, transforming it into a sophisticated health monitoring and alert system with extensive applicability in law enforcement and emergency response scenarios. The processor 1 may be programmed with algorithms to determine an optimal restraint level based on one or more of heart rates, temperature including the difference of temperature between ambient temperature and that of the individual, oxygen levels, vital signs, and tension data, and adjust the restraint mechanism 100 accordingly.

Although the present invention has been illustrated and described herein with reference to preferred embodiments and specific examples thereof, it will be readily apparent to those of ordinary skill in the art that the other embodiments and examples may perform similar functions and/or achieve like results. All such equivalent embodiments and examples are within the spirit and scope of the present invention, are contemplated thereby, and are intended to be covered by the following claims.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Although a preferred embodiment of this invention has been disclosed, a worker of ordinary skill in this art would recognize that certain modifications would come within the scope of this invention. For that reason, the following claims should be studied to determine the true scope and content of this invention.

What is claimed is:

1. A humane restraint device comprising:

a handcuff restraint system with at least two cuff loops connected by a chain;

each cuff loops further comprising a ratchet mechanism paired with a latching mechanism;

a body removably affixed to at least one cuff loop comprising at least one sensor;

the at least one sensor configured to monitor the heart rate of a human being; and a tension monitor configured to measure and detect tension and adjust the level of restraint applied to the human being based on detected tension.

2. The humane restraint device of claim 1, wherein the sensor comprises at least one sensor selected from the group consisting of electrocardiogram (ECG) sensors, pulse oximeters, and photoplethysmography (PPG) sensors.

3. The humane restraint device of claim 1, further comprising a wireless communication module for transmitting heart rate data to an external device.

4. The humane restraint device of claim 2, further comprising a wireless communication module for transmitting heart rate data to an external device.

5. The humane restraint device of claim 3, wherein the heart monitor is configured to generate an alert signal when an abnormal heart rate is detected.

6. The humane restraint device of claim 1, further comprising an alarm integrated into the restraint system, wherein the alarm is configured to generate an alert when an abnormal heart rate is detected.

7. The humane restraint of claim 1, wherein the tension monitor is integrated into the interior surface of the cuff loop of the restraint.

8. The humane restraint of claim 7, wherein the tension monitor is configured to measure tension at multiple points along the restraint.

9. The humane restraint of claim 4, wherein the control unit is programmed with algorithms to determine an optimal restraint level based on heart rate and tension data.

10. The humane restraint of claim 1, further comprising a display integrated on the restraint mechanism.

11. The humane restraint of claim 10, wherein the display further comprises a user interface to control the restraint mechanism.

12. The humane restraint of claim 1, further comprising at least one thermometer at the sensor locations.

13. The humane restraint of claim 12, wherein at least one thermometer is configured to measure the ambient temperature.

14. The humane restraint of claim 12, wherein at least one thermometer is configured to measure the temperature of the restrained person.

15. The humane restraint of claim 13, further comprising at least one thermometer is configured to measure the temperature of the restrained person, and wherein the processor integrates the difference between the temperature of the ambient temperature and the temperature of the restrained person in its algorithms to determine an optimal restraint level.

16. The humane restraint of claim 2, further comprising a perspiration sensor.

17. The humane restraint of claim 7, wherein the cuff loop comprises sensors at multiple locations.

18. The humane restraint of claim 15, wherein the cuff loop comprises sensors at multiple locations.

19. The humane restraint of claim 6, wherein the alarm further alerts if the body is removed from one or more cuff loops.

* * * * *